United States Patent
Ignatius et al.

(10) Patent No.: US 9,506,930 B2
(45) Date of Patent: Nov. 29, 2016

(54) MONITORING AND MANIPULATING CELLULAR TRANSMEMBRANE POTENTIALS USING NANOSTRUCTURES

(75) Inventors: Michael J. Ignatius, Eugene, OR (US); Elena Molokanova, Eugene, OR (US); Alex Savtchenko, Eugene, OR (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 983 days.

(21) Appl. No.: 13/606,434

(22) Filed: Sep. 7, 2012

(65) Prior Publication Data

US 2013/0033252 A1 Feb. 7, 2013

Related U.S. Application Data

(63) Continuation of application No. 12/651,221, filed on Dec. 31, 2009, now Pat. No. 8,290,714, which is a continuation of application No. 11/371,465, filed on Mar. 8, 2006, now abandoned.

(60) Provisional application No. 60/659,975, filed on Mar. 8, 2005.

(51) Int. Cl.
| | |
|---|---|
| *A61K 38/12* | (2006.01) |
| *G01N 33/68* | (2006.01) |
| *B82Y 5/00* | (2011.01) |
| *B82Y 15/00* | (2011.01) |
| *G01N 33/58* | (2006.01) |

(52) U.S. Cl.
CPC .............. *G01N 33/6872* (2013.01); *B82Y 5/00* (2013.01); *B82Y 15/00* (2013.01); *G01N 33/588* (2013.01)

(58) Field of Classification Search
None
See application file for complete search history.

(56) References Cited

U.S. PATENT DOCUMENTS

| | | | |
|---|---|---|---|
| 5,505,928 A | 4/1996 | Alivisatos et al. |
| 5,990,479 A | 11/1999 | Weiss et al. |
| 6,114,038 A | 9/2000 | Castro et al. |
| 6,194,213 B1 | 2/2001 | Barbera-Guillem |
| 6,207,229 B1 | 3/2001 | Bawendi et al. |
| 6,207,392 B1 | 3/2001 | Weiss et al. |
| 6,251,303 B1 | 6/2001 | Bawendi et al. |
| 6,274,323 B1 | 8/2001 | Bruchez et al. |
| 6,287,758 B1 | 9/2001 | Okun et al. |
| 6,306,610 B1 | 10/2001 | Bawendi et al. |
| 6,319,426 B1 | 11/2001 | Bawendi et al. |
| 6,322,901 B1 | 11/2001 | Bawendi et al. |
| 6,326,144 B1 | 12/2001 | Bawendi et al. |
| 6,423,551 B1 | 7/2002 | Weiss et al. |

(Continued)

FOREIGN PATENT DOCUMENTS

| | | |
|---|---|---|
| WO | WO-01/59446 | 8/2001 |
| WO | WO-2004/034025 | 4/2004 |

OTHER PUBLICATIONS

Alivisatos, A. P., "Perspectives on the Physical Chemistry of Semiconductor Nanocrystals", *The Journal of Physical Chemistry*, vol. 100, No. 31, 1996, 13226-13239.

(Continued)

*Primary Examiner* — Anna Skibinsky

(57) ABSTRACT

The use of nanostructures to monitor or modulate changes in cellular membrane potentials is disclosed. Nanoparticles having phospholipid coatings were found to display improved responses relative to nanoparticles having other coatings that do not promote localization or attraction to membranes.

18 Claims, 3 Drawing Sheets

(56) References Cited

U.S. PATENT DOCUMENTS

| | | |
|---|---|---|
| 6,426,513 B1 | 7/2002 | Bawendi et al. |
| 6,444,143 B2 | 9/2002 | Bawendi et al. |
| 6,500,622 B2 | 12/2002 | Bruchez, Jr. et al. |
| 6,537,771 B1 | 3/2003 | Farinas et al. |
| 6,548,168 B1 | 4/2003 | Mulvaney |
| 6,576,291 B2 | 6/2003 | Bawendi et al. |
| 6,649,138 B2 | 11/2003 | Adams et al. |
| 6,699,723 B1 | 3/2004 | Weiss et al. |
| 6,815,064 B2 | 11/2004 | Treadway et al. |
| 2004/0110123 A1 | 6/2004 | Maher et al. |

OTHER PUBLICATIONS

Bruchez, M et al., "Semiconductor Nanocrystals as Fluorescent Biological Labels", *Science*, vol. 281., Sep. 25, 1998, 2013-2016.
Brueggemann, A. et al., "Ion Channel Drug Discovery and research: The Automated nano-Patch-Clamp Technology", *Current Drug Discovery Technologies*;1(1), 2004, 91-96.
Brueggemann, A. et al., "Ion Channel drug discovery and research: the automated nano-patch-clamp technology", *Curr. Drug Discov. Tech.*, Jan. 1, 2004, 91-96.
Chan, et al., "Quantum Dot Bioconjugates for Ultrasensitive Nonisotopic Detection", *Science*, vol. 281, No. 5385, Sep. 25, 1998, pp. 2016-2018.
Dahan, M. et al., "Diffusion Dynamics of Glycine Receptors Revealed by Single-Quantum Dot Tracking", *Science*;317(2), Oct. 17, 2003, 442-445.
Dahan, M. et al., "Diffusion Dynamics of Glycine Receptors Revealed by Single-Quantum Dot Tracking", *Science*, vol. 302, Oct. 17, 2003, 442-445.
Dubertret, Benoit et al., "In Vivo Imaging of Quantum Dots Encapsulated in Phospholipid Micelles", *Science*, vol. 298, Nov. 29, 2002, 1759-1762.
Fernandez, Marta et al., "Lipoid pH indicators as probes of electrical potential and polarity in micelles", *J. Phys. Chem., 81* (18)., 1977, 1755-1761.
Fromherz, Peter et al., "Silicon-Neuron Junction: Capacitive Stimulationof an Individual Neuron on a Silicon Chip", *Phys. Rev. Lett.*, 1995, 1670-1673.
Hao, E. et al., "Electromagnetic Fields Around Silver Nanoparticles and dimers", *Journal of Chem. Phy*;120(1), Jan. 1, 2004, 357-366.
Hao, E. et al., "Synthesis and Optical Properties of Anisotropic Metal Nanoparticles", *Journal of Fluorescence*; 14(4), Jul. 2004, 331-341.
Jaiswal, J. et al., "Long-Term Multiple Color Imaging of Live Cells Using Quantum Dot Bioconjugates", *Nature Biotechnology*, Jan. 21, 2003, 47-51.
Kagan, C R. et al., "Long-range resonance transfer of electronic excitations in close-packed CdSe quantum-dot solids", *Physical Review B*, vol. 54, No. 12, Sep. 15, 1996, 8633-8643.
Kloepfer, J. A. et al., "FRET between CdSe quantum dots in lipid vesicles and water—and lipid-soluble dyes", *Journal of Physical Chemistry B 20041104 American Chemical Society US*, vol. 108, No. 44, Nov. 4, 2004, 17042-17049.
Li, N. et al., "Biology on a chip: Microfabrication for styding the behavior of cultured cells", *Critical Reviews in Biomedical Engineering*, vol. 31, No. 5&6, 2003, 423-488.
Starovoytov, A. et al., "Light-Directed Electrical Stimulation of Neurons Cultured on Silicon Wafers", *J. of Neurophysiol*; 93, Sep. 22, 2004, 1090-1098.
Stroscio, M. et al., "Intergrated biological-semiconductor devices", *Proceedings of the IEEE*, 93(10), Oct. 2005, 1772-1783.
Watson, A. et al., "Lighting Up Cells with Quantum Dots", *Biotechniques*; 34(2), Feb. 1, 2003, 296-303.
Winter, J. et al., "Optimization of quantum dot—Nerve cell interfaces", *Materials Research Society Symposium—Proceedings Materials Research Society Symposium—Proceedings—Quantum Dots, Nanoparticles and Nanowires*, Materials Research Society US, vol. 789,2003, 2003, 119-122.
Winter, J. O. , "Development and Optimization of Quantum Dot-Neuron Interfaces", *Dissertation presented to the faculty of the graduate school of the universtiy of Texas at Austin*, 2004.
Winter, J. O. et al., "Quantum dots for electrical stimulation of neural cells", *Progress in Biomedical Optics and Imaging of SPIE—Nanobiophotonics and Biomedical Applications*, SPIE US,vol. 5705, 2005, 235-246.
Winter, J. O. et al., "Recognition molecule directed interfacing between semiconductor quantum dots and nerve cells", *Advanced Materials 20011116 Wiley-VCH Verlag DEU*, vol. 13, No. 22, Nov. 16, 2001, 1673-1677.
WO 2006/096835, , "PCT IPRP mailed Sep. 12, 2007".
WO 2006/096835 , , "PCT ISR mailed Sep. 13, 2006", Sep. 13, 2006.
Wolff, C. et al., "Comparative Study of Membrane Potential-Sensitive Fluorescent Probes and their Use in Ion Channel Screening Assays", *J Biomol Screen*, 8, 2003, 533-543.
Zorov, et al., "Examining Intracellular Organelle Function Using Fluorescent Probes From Animalcules to Quantum Dots", *Circulation Research*, vol. 95, 2004, 239-252.

MONITORING AND MANIPULATING CELLULAR TRANSMEMBRANE POTENTIALS USING NANOSTRUCTURES

CROSS REFERENCE TO RELATED APPLICATIONS

The present application is a continuation of U.S. patent application Ser. No. 12/651,221, filed Dec. 31, 2009, now U.S. Pat. No. 8,290,714, which is a continuation of U.S. patent application Ser. No. 11/371,465, filed Mar. 8, 2006, which claims priority to U.S. Provisional Patent Application Ser. No. 60/659,975 filed Mar. 8, 2005, the contents of which are incorporated herein by reference in their entirety.

FIELD OF THE INVENTION

The invention relates to compositions and methods useful for monitoring and manipulating cellular transmembrane voltages. In particular, nanoparticles and their use in monitoring and manipulating transmembrane voltages is disclosed.

DESCRIPTION OF RELATED ART

All cells have phospholipid membranes that serve as bimolecular barriers and to separate cell contents from the extracellular environment. The purpose of the plasma membrane is to maintain the necessary difference in composition between two compartments by restricting or permitting the passage of materials through the membrane as a function of intracellular signaling.

Each cell has a resting membrane potential originating from the so-called "separation of charge" across the normally impermeable phospholipid bilayer. Because of unequal distribution of positively and negatively charged ions in the extracellular and intracellular compartments, all living cells have a negative resting membrane potential, ranging from −5 mV to 100 mV. The ion permeability of the plasma membrane is determined by the presence of ion channels, transmembrane proteins specialized in passive ion transport. Membrane potential can be changed by changing membrane permeability to as certain ion in response to an activating stimulus, thus allowing a flux of ions down their electrochemical gradient. Transport of ions across the membrane through ion channels will lead to disturbance of the existing equilibrium of ion concentrations on both sides of membrane and, thus, to changes of electrical properties of the cell.

Cells communicate with each other through changes in membrane potential. Therefore, monitoring the cellular membrane potential and its changes allows monitoring of cell viability and function.

Ion channels are transmembrane proteins present in both excitable and non-excitable cells. Ion channels permit and regulate movement and conduction of ions down their electrochemical gradients across a normally ion-impermeant lipid bilayer. They produce electrical signals leading to action potential generation that controls a number of key processes, including neuronal signaling, heart beat, brain function, sensory transduction and muscle contraction. In addition to setting the resting membrane potential and controlling cellular excitability, these transmembrane proteins play important roles affecting the physiological state of cells by being involved in cell proliferation, hormone secretion and homeostasis of water and electrolytes.

Activation of ion channels by any mechanism results in redistribution (changes in concentrations) of intracellular extracellular ions and consequent change in cellular membrane potential. Thus, recording changes in membrane potential allows direct monitoring of ion channel activity.

A typical organism has hundreds to thousands of different types of ion channels, while an individual cell can have ten to twenty different types. Each ion channel exhibits high selectivity for one or a few ion species.

Different ion channel families are classified based on their activation stimuli, selectivity to different ions, inactivation mechanisms and pharmacological profiles. There are voltage-activated and ligand-activated ion channels. Superfamilies of voltage-gated sodium, potassium, calcium, and chloride ion channels have been defined using electrophysiological, pharmacological and molecular techniques; they are named according to their selective permeability for a particular cation with reference to their voltage dependence, kinetic behavior or molecular identity. Superfamilies of ligand-gated channels are much less structurally related and named after their activation ligand, i.e. cyclic nucleotide-gated channels or GABA channels.

Functionally, the opening or closing of ion channels can be controlled or "gated" by the binding of signaling molecules (ligand-gated channels), by a change in the membrane potential (voltage-gated channels), or by mechanical stimulation (mechanosensitive channels) that results in conformational changes within ion channel structures leading to opening of a pore and allowing a flux of ions inside or outside the cell.

For example, a voltage-gated sodium channel is closed at a resting membrane potential below −60 mV, and opens upon depolarization of the membrane (i.e., a shift in the membrane potential to a less negative value).

The structures of voltage-gated sodium, calcium and potassium channels have common functional elements. All ion channels are transmembrane proteins comprised of several homologous repeats arranged around a common ion-selective aqueous pore that opens in response to an activating stimulus that allows ions to enter or exit the cell. Each repeat consists of six transmembrane domains (S1-S6) with the S4 domain playing the specialized role of voltage sensor. Channel opening and closing ("gating") is controlled by this voltage sensitive domain of the protein containing charged amino acids that respond to changes in the electric field. Translocation of a voltage sensitive domain leads to conformational changes in the structure of the channel resulting in conducting (open/activated) or non-conducting (closed/inactivated) states.

Although ligand-gated channels differ significantly from one another, there are two structural elements present in every channel: a ligand-binding domain and a pore domain. Binding of a specific ligand triggers conformational changes leading to opening of the pore domain and allowing the ion flux into/out of the cell, which is reflected in a change in transmembrane potential.

The various states of ion channel activation provide unique opportunities for more efficient drug discovery, enabling state-dependent molecules to be developed that, for example, only bind to non-conducting (inactivated) channels. A desirable goal is to target drugs to tissues exhibiting abnormal electrical activity, while leaving normal channels in active tissues unaffected. Also, identifying new ion channels, testing their functions, and validating them as drug targets are current efforts of many biotech companies and academic researchers.

Ion Channels in Drug Discovery

Ion channels are of particular importance in the pharmaceutical industry in two areas: ion channels as drug targets and ion channel safety pharmacology. Ion channels are significant targets in the drug discovery process, generating several billion dollars in sales per annum. Abnormal ion channel function or ion channel expressions have been linked to a number of therapeutic areas (i.e. cardiac arrhythmia, hypertension, epilepsy, pain). Ion channel modulator drugs for these have yet to be developed. Many pharmaceutical companies have active ion channel drug development projects or programs. Additionally, a number of biotech or biopharmaceutical companies focus exclusively on ion channel drug development (ChanTest, Cleveland, Ohio; BioFocus, Cambridge, UK; Icagen, Durham, N.C.).

Ion channels are involved in many vital functions, and any dysfunction of ion channels caused by changes in biochemical regulation, expression levels, or structural mutations can impact the well-being of living organisms. In humans, inherited or induced changes in ion channel function could result in serious complications to health. Several disease states are related to dysfunctional ion channels. Ion channel defects produce a clinically diverse set of disorders that vary from cystic fibrosis and some forms of migraine to renal tubular defects and episodic ataxias.

In particular, ion channels have been implicated in cardiac arrhythmias, familial periodic paralyses, cystic fibrosis, epilepsy, diabetes, asthma, angina pectoris, malignant hyperthermia, pain, hypertension, epilepsy, etc. Ion channels represent key molecular targets for drug discovery. Pharmaceutical and biotechnology companies have successfully targeted ion channels in their bid to make new more effective drugs. Now various ion channel blockers or openers are being used and evaluated as therapeutic drugs for a variety of diseases.

Voltage-gated calcium ion channels are involved in numerous cellular functions, and their role in generating a defined disease phenotype is complex. Certain types of calcium-channels may play a role in nociception and migraine pathophysiology. In human medicine, calcium-channel blockers are being evaluated for, among other things, treating glaucoma, deep vein thrombosis, and pulmonary hypertension, in renal transplantation, and for prevention of perfusion injury.

Several voltage-dependent calcium channels blockers have been shown to be effective in inhibiting pain. Furthermore, blockage of so-called non-L-type calcium channels was found to exert therapeutic effects in the treatment of severe pain and ischemic stroke.

Dysfunction of potassium channels has been associated with the pathophysiology of a number of neurological, as well as peripheral, disorders (e.g., episodic ataxia, epilepsy, neuromyotonia, Parkinson's disease, congenital deafness, long QT syndrome).

Activation of potassium ion channels generally reduces cellular excitability, making potassium-channel openers potential drug candidates for the treatment of diseases related to hyperexcitability such as epilepsy, neuropathic pain, and neurodegeneration.

Most notably, mutations of the HERG potassium ion channels expressed in cardiac tissues or pharmacological blockage of HERG channels cause heart disease (long Q-T syndrome), which leads to increased risk of ventricular tachycardia and sudden death. Several drugs affect these channels and can lead to life threatening cardiac arrhythmias. In this perspective, drug discovery companies usually find it necessary to evaluate each of their drug candidates for interference with these channels. Thus, many companies conduct HERG testing before any further investigation is carried out.

The dynamic nature of sodium ion channel expression makes them important targets for pharmacological manipulation in the search for new therapies for pain. For example, mutations in the gene encoding the alpha subunit of sodium-channels have been linked to paroxysmal disorders such as epilepsy, long QT syndrome, hyperkalemic periodic paralysis in humans and to motor endplate disease and cerebellar ataxia in mice. Voltage-gated sodium ion channel have been shown to be key mediators of the pathophysiology of pain. One of the most frequently used anesthetic drugs used is Lidocaine which inhibits sodium ion channels. Changes in brain sodium-channels may be a cause of central pain, and further, abnormal expression of sodium-channel genes and its contributions to hyperexcitability of primary sensory neurons have been discussed. Recently, sensory-neuron-specific (SNS) TTX-resistant sodium-channels have been examined for their role in nociception and pain. This study suggests that blockage of SNS expression or function may produce analgesia.

Experimental Approaches for Ion Channel Research

The preferred method for studying ion channels is the patch clamp method (Neher, E. and Sakmann, B., *Nature* 260(5554): 799-802 (1976); Hamill, O. P., et al., *Pflugers Arch.* 391(2): 85-100 (1981)).

This technique consists of contacting a cell with the tip of a very clean glass micropipette (diameter of about 1 μm), and obtaining a high resistance seal (leakage resistance>1 GOhm, GigaSeal) between the glass and the cell surface by applying gentle suction. Next, by applying greater suction or a large voltage, it is possible to break the intra-pipette portion of membrane and thereby make direct electrical contact between the cell interior and the pipette electrode (whole-cell configuration of patch clamp method). Different voltages can then be applied to the pipette electrode, and the currents measured represent the current through the cell membrane, which includes the integral current through the ion channels present.

To date, the patch-clamp method has been considered the industry gold standard for monitoring ion channel activity. The patch-clamp directly records ion channel activity, has sub-millisecond temporal resolution, very high information content and is extremely sensitive including the ability to study "single" ion channels. Due to its high information content, patch-clamp-based screening has very low rate of "false negatives" and "false positives".

Although this technique allows detailed biophysical characterization of ion channel activation, inactivation, gating, ion selectivity, and drug interactions, throughput is quite low and ease-of-use of patch-clamp instrumentation is generally unsatisfactory for effective mass screening. The demands of ion channel high throughput screening ("HTS") include robust instrumentation and high signal-background ratio combined with satisfactory ease-of-use. Historically, ion channel HTS is equated with low information content, emphasizing the need for novel rapid and easy methods in which more useful information can be gathered about membrane potential changes in various cell types.

Ion Channel HTS Approaches

Traditionally, HTS technologies employed for ion channel primary screening rely on binding assays, ion-flux assays and fluorometric approaches. Until now the most significant task for these methods has been to generate enough HTS data with acceptable information content and reliability.

The search for molecules that modulate ion channel function has been hindered by the lack of direct electrical measurements in HTS formats. Membrane excitability in cell-based assays is a dynamic phenomenon that requires fast, precise and accurate measurements to gather high information content data. Real-time measurements of transmembrane potential kinetics that accurately reflect ion channel activity are fundamental to cell physiology, but are difficult to measure in existing HTS format methods.

Reliable and robust high HTS assays for ion channels are important in ion-channel based drug discovery. Ion channels are dynamic proteins, and therefore require assays that "sense" their various functional states. Competition-binding assays, although successfully used for other target classes, often fail to identify ligands that modulate specific ion channel states. Cell-based functional assays, therefore, are preferred for HTS of ion channel targets.

Currently Available Assays

Modern technologies employed for ion channel screening include: binding assays, ion flux assays, fluorometric imaging and electrophysiology.

Binding assays for cell surface receptors are used in screen development and primary screening. This type of assay is frequently carried out using scintillation proximity assay (SPA) or fluorescence detection techniques, which have replaced the older radiolabelled ligands and filtration assays. The SPA technique relies upon excitation of a scintillant microbead upon binding of a radiolabelled ligand to a receptor immobilized on the surface of the bead.

Fluorescence spectrometry is used to measure the binding equilibrium between a fluorophore-labeled ligand and receptor. Unfortunately binding assays only detect binding of compounds to ion channels and do not reveal changes in target function, such as modulation of ion channel kinetics.

Optical readouts of ion channel function are favorable for HTS because they are versatile, amenable to miniaturization and automation and potentially sensitive.

Fluorescence readouts are used widely both to monitor intracellular ion concentrations and to measure membrane potentials. For example, large transient increases in intracellular calcium concentration through activation of ion channels can be monitored using fluorescent probes such as Fluo-3 and Calcium Green. In addition to ion-selective fluorescent indicators, there are several fluorescent dyes that are sensitive to changes in membrane potential, including styryl, bisoxonol, and fluorescence resonance energy transfer-based voltage-sensitive dyes.

For example, the fluorescent dye bis-(1,3-dibutylbarbituric acid) trimethine oxonol, or DiBAC4(3), has been the reagent of choice for measuring membrane potential in HTS formats. Redistribution of the dye in the cellular membrane as a result of depolarizing or hyperpolarizing stimuli in cells causes changes in fluorescence. However, utilization of DiBAC4(3) has several limitations, including slow kinetics (in the seconds to minutes range) and fluctuations in response to changes in temperature and concentration of the dye. In addition, screening experiments using bisoxonol dyes require multi-step procedures and take 30-60 min for dye loading, potentially compromising the fidelity and reducing throughput of DiBAC4(3)-based screening assays.

HTS Patch-Clamp

The patch clamp technique is widely used to study currents through ion channels. The whole-cell patch-clamp is used today in tertiary screening of selected lead molecules in late stages of the drug discovery process. Whole-cell patch-clamp, however, is not suitable for initial high throughput screening.

Although very powerful, this technique is labor-intensive and, therefore, limited to few data point measurements per day. This low throughput has encouraged the use of other less specific and less sensitive technologies for high-throughput screening of ion channel targets.

Optimal HTS Ion Channel Assay Requirements

In high-throughput screening campaigns (200,000+ samples), binding assays remain the first choice in terms of throughput and cost. This reflects the technical ease of performing these types of assays and, hence, their ability to be automated. However, in modern ion channel drug discovery screening, there is a trend toward use of cellular-based functional assays as primary screening tools.

Cellular functional assays are used as primary or secondary assays to determine functionality of compounds from a binding screen and also to assess toxicity. These types of assays are information rich and therefore potentially of significant value in drug discovery.

Identifying targets and putative drug candidates by obtaining as much knowledge as possible per experiment about the effects of each compound is the ultimate goal for initial ion channel screening.

Voltage Sensitive Probes

Currently used fluorescent voltage sensor dyes, which respond to potential-dependent accumulation and redistribution across the cellular membrane, are limited to steady-state assays of membrane potential. This is because the fluorescence response of these dyes occurs minutes after the change in membrane potential. Since voltage sensor dyes are charged they also interfere with the membrane potential caused by the ionic current; to reduce this signal-to-noise effect the dye concentration has to be kept below a certain level. Thus, redistribution-based voltage sensor dyes are prone to false-negatives. In addition, compound-voltage dye interactions can show high false-positive rates.

Voltage-sensing Fluorescence Resonance Energy Transfer (FRET) acceptors, for example coumarin-tagged phospholipids integrated into the cell membrane ameliorate many of the problems associated with standard voltage sensors, allowing sub-second kinetic determination. Using high throughput screening FRET-based voltage sensors a throughput of several 96-well plates per hour can be performed with the Voltage Ion Probe Reader (VIPR™), a product developed by Aurora BioSciences (now Vertex Pharmaceuticals, Inc.; Cambridge, Mass.).

Compared with results obtained with traditional patch-clamp method, VIPR assays are less sensitive. The temporal resolution in fluorescence-based ion-channel assays using voltage-sensor dyes reduces the accessible kinetic range relative to patch-clamp-based ion channel assays.

Ion-specific fluorescent probes for intracellular ions have been shown to be useful for ion channel screening. Depending on the application, a number of different dyes are available with different ranges of affinities, of which fluorescent calcium indicators are the most commonly used. A significant disadvantage of calcium dye-based ion-channel assays is their slow kinetic resolution of changes of intracellular calcium concentration, due to uncontrolled or unpredictable cellular processes. This can interfere with assay results. To achieve high throughput and low noise, FLIPR-type fluorescent readers are commonly used in conjunction with calcium specific dyes. So far only assays involving measurements of calcium channel activity or other non-selective cation channels have proven to be robust enough for effective HTS efforts.

In summary, an optimal HTS ion channel screening method would have high temporal resolution, high sensitivity and high information content, resulting in low rates of "false negatives" and "false positives". Despite the materials and methods available to study ion channels, there exists a need for new materials and methods that are easy, robust, and useful.

Nanoparticles or Nanocrystals

Numerous studies have been published describing nanoparticles and methods for their use. Semiconductor nanocrystals are sometimes referred to as "Quantum Dots" or "QDots", although these are registered trademarks of Quantum Dot Corporation (a wholly owned subsidiary of Invitrogen Corp.; Carlsbad, Calif.). Nanoparticles are typically spherical or nearly so, having a central core, a surrounding shell, and optional capping groups, linkers, and other surface-conjugated materials.

Semiconductor nanoparticles are nanometer-scale crystals composed of hundreds to thousands of atoms of an inorganic semiconductor material in which electron-hole pairs can be created and confined.

Specific optical properties of nanoparticles are based on the mechanism of quantum confinement. Quantum confinement is the trapping of electrons or electron "holes" (charge carriers) in a space small enough that their quantum (wavelike) behavior dominates their classical (particle-like) behavior.

In nanoparticles, where motions of electrons holes are highly limited in three dimensional space, quantum confinement results in a strong increase of optical excitation energies compared to the bulk semiconductor material. For quantum confinement to occur, the dimension of the confining device or particle must be comparable to the electron-hole Bohr radius of the material it is made from. After electron-hole pairs in the core of a nanocrystal are formed upon excitation with light, they can recombine and re-emit light having a narrow and symmetric emission spectrum that depends directly on the size of the crystal. The smaller the nanoparticle core, the bigger the bandgap between the valence and conduction bands, the bluer the emitted photon; and vice versa (redder emission) for larger nanoparticles.

Commercially available semiconductor nanocrystals are comprised of several layers, including a core, an inorganic lattice-matching crystalline shell (to improve the nanocrystal's optical properties and possibly serving to minimize cytotoxicity), and a coating or coatings (to allow water compatibility and for effective interaction with modifiers such as biomacromolecules).

Nanocrystals are used in information technology (the quantum computer), light emitting diodes, lasers, and telecommunication devices, bar coding, photodetectors, optical switching, and thermoelectric devices. Recently, nanocrystals have been used for cell labeling, cell tracking, in vivo imaging, DNA detection, protein labeling, and in other detection modes.

Nanocrystals have excellent optical properties as biological optical sensors, including size-tunable emission, narrow spectral width, broad excitation spectrum, high quantum yields, high two-photon cross-section, and low photobleaching rates.

However, until now biological and biotechnological applications of nanocrystals have been mostly limited to their use as biomarkers rather than as detectors of biological processes.

Applications of nanocrystals in industry include, for example, nanocrystal-based electro-luminescent devices capable of emitting light of various wavelengths in response to external stimuli, where variations in applied voltage could result in change of color of the light emitted by the device.

Many patents and patent publications report nanocrystal compositions, methods for their preparation, and methods for their use. The following collection is a sampling of the research done to date.

U.S. Pat. No. 5,505,928 (issued Apr. 9, 1996) describes methods of preparing III-V semiconductor nanocrystal materials. Examples of such materials include GaAs, GaP, GaAs—P, GaSb, InAs, InP, InSb, AlAs, AlP, and AlSb. The produced materials can be 1-6 nm in size, and are relatively monodisperse.

U.S. Pat. No. 5,990,479 (issued Nov. 23, 1999) describes nanocrystals linked to affinity molecules. Listed affinity molecules include monoclonal and polyclonal antibodies, nucleic acids, proteins, polysaccharides, and small molecules such as sugars, peptides, drugs, and ligands.

U.S. Pat. No. 6,114,038 (issued Sep. 5, 2000) describes water soluble, functionalized nanocrystals having a capping compound of the formula $HS(CH_2)_nX$, wherein X is a carboxylate. The nanocrystals also have a diaminocarboxylic acid which is operably linked to the capping compound.

U.S. Pat. No. 6,207,229 (issued Mar. 27, 2001) describes a coated nanocrystal capable of light emission includes a substantially monodisperse nanoparticle selected from the group consisting of CdX, where X=S, Se, or Te; and an overcoating of ZnY, where Y=S, or Sc. Methods of preparing the nanocrystals using a first semiconductor core and a precursor capable of thermal conversion into a second semiconductor material that forms a coating layer over the core.

U.S. Pat. No. 6,207,392 (issued Mar. 27, 2001) describes semiconductor nanocrystals having one or more attached linking agents. The nanocrystals can include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs.

U.S. Pat. No. 6,251,303 (issued Jun. 26, 2001), U.S. Pat. No. 6,319,426 (issued Nov. 20, 2001) and U.S. Pat. No. 6,444,143 (issued Sep. 3, 2002) describe a water-soluble semiconductor nanocrystal. The outer layer of the nanocrystal contains a molecule having at least one linking group for attachment of the molecule to the overcoating shell layer, and at least one hydrophilic group optionally spaced apart from the linking group by a hydrophobic region sufficient to prevent electron charge transfer across the hydrophobic region.

U.S. Pat. No. 6,274,323 (issued Aug. 14, 2001) describes a method of detecting a polynucleotide in a sample, using a semiconductor nanocrystal in an immunosorbant assay.

U.S. Pat. No. 6,306,610 (issued Oct. 23, 2001) describes semiconductor nanocrystals having attached multidentate ligands. The nanocrystals can be associated with various biological molecules such as proteins and nucleic acids.

U.S. Pat. No. 6,322,901 (issued Nov. 27, 2001) describes monodisperse coated nanocrystals that emit light in a spectral range of no greater than about 60 nm full width at half max (FWHM). The spectral range of the nanocrystals is about 470 nm to about 620 nm, and the particle size of the nanocrystal core is about 20 angstroms to about 125 angstroms.

U.S. Pat. No. 6,326,144 (issued Dec. 4, 2001) describes semiconductor nanocrystals linked to various compounds using a linker of structure $H_zX((CH_2)_nCO_2H)_y$, and salts thereof, where X is S, N, P or O=P; n is greater than or equal to 6; and z and y are selected to satisfy the valence requirements of X.

U.S. Pat. No. 6,423,551 (issued Jul. 23, 2002) and U.S. Pat. No. 6,699,723 (issued Mar. 2, 2004) describe a water soluble semiconductor nanocrystal having a linking agent capable of linking to an affinity molecule. A list of affinity molecules includes monoclonal and polyclonal antibodies, nucleic acids (both monomeric and oligomeric), proteins, polysaccharides, and small molecules such as sugars, peptides, drugs, and ligands. Examples of linking agents include N-(3-aminopropyl)3-mercapto-benzamide, 3-aminopropyl-trimethoxysilane, 3-mercaptopropyl-trimethoxysilane, 3-maleimidopropyl-trimethoxysilane, and 3-hydrazidopropyl-trimethoxysilane.

U.S. Pat. No. 6,426,513 (issued Jul. 30, 2002) describes a water-soluble semiconductor nanocrystal comprising a quantum dot having a selected band gap energy; an overcoating layer comprising a material having a band gap energy greater than the band gap energy of the quantum dot; and an outer layer comprising a compound having a formula, $SH(CH_2)_nX$, where X is carboxylate or sulfonate, and n is greater than or equal to 8.

U.S. Pat. No. 6,500,622 (issued Dec. 31, 2002) describes semiconductor nanocrystals having attached polynucleotide sequences. The nanocrystals can be used to determine the presence or absence of a target sequence in a sample. The nanocrystal can be identified using a spectral code.

U.S. Pat. No. 6,548,168 (issued Apr. 15, 2003) describes a method of stabilizing particles with an insulating, semi-conducting and/or metallic coating. A particle-coating admixture containing a bifunctional ligand is used to bind a particle to the coating. Examples of bifunctional ligands include 3-mercaptopropyl trimethoxysilane ("MPS"), 1,3-propanedithiol, 3-aminopropanethiol ("APT"), and 3-amino propyl trimethoxysilamine ("APS").

U.S. Pat. No. 6,576,291 (issued Jun. 10, 2003) describes a method of manufacturing a nanocrystallite, the method comprising contacting a metal, M, or an M-containing salt, and a reducing agent to form an M-containing precursor, M being Cd, Zn, Mg, Hg, Al, Ga, In, or Tl; contacting the M-containing precursor with an X donor, X being O, S, Se, Te, N, P, As, or Sb to form a mixture; and heating the mixture in the presence of an amine to form the nanocrystallite. The nanocrystallites can be used in a variety of applications including optoelectronic devices including electroluminescent devices such as light emitting diodes (LEDs) or alternating current thin film electroluminescent devices (ACTFELDs).

U.S. Pat. No. 6,649,138 (issued Nov. 18, 2003) describes a water-dispersible nanoparticle comprising: an inner core comprised of a semiconductive or metallic material; a water-insoluble organic coating surrounding the inner core; and, surrounding the water-insoluble organic coating, an outer layer comprised of a multiply amphipathic dispersant molecule, wherein the dispersant molecule comprises at least two hydrophobic regions and at least two hydrophilic regions. The nanoparticles can be conjugated to various affinity molecules, allowing use in applications such as fluorescence immunocytochemistry, fluorescence microscopy, DNA sequence analysis, fluorescence in situ hybridization (FISH), fluorescence resonance energy transfer (FRET), flow cytometry (Fluorescence Activated Cell Sorter; FACS) and diagnostic assays for biological systems.

U.S. Pat. No. 6,815,064 (issued Nov. 9, 2004) describes a nanoparticle containing a Group 2 element, a Group 12 element, a Group 13 element, a Group 14 element, a Group 15 element, a Group 16 element, Fe, Nb, Cr, Mn, Co, Cu, or Ni in an inorganic, shell around the semiconductor core. The compositions and methods of preparation are proposed to facilitate the overgrowth of a high-quality, thick shell on a semiconductive core by compensating for the mismatching of lattice structures between the core and shell materials.

Despite the materials and methods available to study ion channels, there exists a need for new materials and methods that are easy, robust, and useful. Additionally, there is a need for methods of controlling the membrane potential of cells to facilitate studying the effects of administered materials.

SUMMARY OF THE INVENTION

The use of nanostructures to measure or modulate changes in cellular or subcellular membrane potentials is disclosed. Nanostructures associated with cells respond to changes in membrane potential, and can be easily monitored. The methods can be used to monitor the effects of added external agents on cellular membrane potential.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

DETAILED DESCRIPTION OF THE INVENTION

Figure 1:
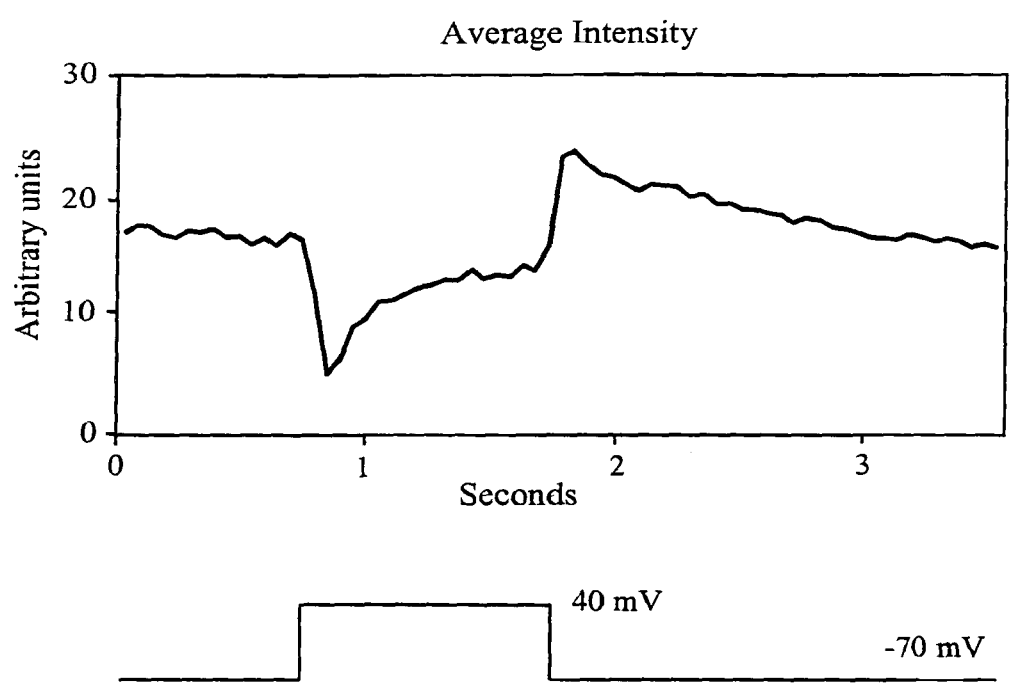
FIG. 1 shows the effect of electrophysiological stimulation on cells containing intracellular nanoparticles. The upper trace shows the change in fluorescence intensity of semiconductor nanocrystals inside the cell in response to change in transmembrane potential using the patch-clamp method. The x-axis is time in seconds; the y-axis is Arbitrary Units. Semiconductor nanocrystals were loaded inside cell through patch pipette. The lower trace represents the corresponding voltage stimulation protocol along the same time scale.

While compositions and methods are described in teams of "comprising" various components or steps (interpreted as meaning "including, but not limited to"), the compositions and methods can also "consist essentially of" or "consist of" the various components and steps, such terminology should be interpreted as defining essentially closed-member groups.

Methods of Assaying Changes in Transmembrane Potential

One embodiment of the invention is directed towards methods for assaying a change in transmembrane potential. The methods can comprise providing at least one target, wherein the target is a cell, cellular fraction, or artificial membrane structure; contacting the target with at least one nanostructure to form a treated target; stimulating the treated target; assaying emission from the nanostructure; and correlating the emission with the change in transmembrane potential. An optional additional step can comprise assaying emission from the nanostructure after the contacting step but before the stimulating step. This additional step can act as a "control" or "blank" measurement.

The target can be one or more intact cells, can be one or more cellular fractions, or one or more artificial membrane structures. Examples of cellular fractions include any luminal organelles such as nucleus, ribosomes, mitochondria, endoplasmic reticulum, Golgi apparatus, vacuoles, synaptic vesicles and lysosomes. Examples of the artificial membrane structures include phospholipid micelles, micro- and nanocapsules and semi-liquid films supportive structures. The contacting step can comprise introducing the nanostructure into the target. Alternatively, the contacting step can comprise introducing the nanostructure into a cellular membrane of the target. The nanostructure can alternatively be introduced onto or near a cellular membrane of the target. Nanostructures "near" the target are sufficiently close in proximity so as to be able to detect changes in transmembrane potential. As an example, nanostructures closer than about 100 microns are sufficiently near a target so as to have this property.

The target can be stimulated by a wide variety of methods. Examples of such stimulation methods include electrical stimulation, magnetic stimulation, chemical stimulation, biological stimulation, or combinations thereof. Examples of electrical stimulation include the use of a patch clamp, and application of an external electric field. Examples of chemical stimulation include contacting the target with a potassium salt or a sodium salt, or with different types of intramembrane pore-forming molecules. Examples of biological stimulation include activating the target with a light-sensitive ion channel, or contacting the target with the chemical entities, acting as modifiers of ion channel activity. Examples of magnetic stimulation include activating the target with alternating electromagnetic field of the appropriate frequency and amplitude.

Targets can be electrically stimulated by a variety of methods. One stimulation protocol (voltage amplitudes and duration of stimulation) is often chosen based on activation kinetics of the ion channel of interest. For example, targets can be maintained at a first membrane potential voltage, subjected to a depolarizing pulse at a second membrane potential voltage, and returned to the first membrane potential voltage. The second membrane potential voltage is typically more positive than the first membrane potential voltage, but it is possible that the first membrane potential voltage is more positive than the second membrane potential voltage. For example, the first membrane potential voltage can be negative, while the second membrane potential voltage can be positive. An example is −70 mV for the first membrane potential voltage, and +40 mV for the second membrane potential voltage. Alternatively, the first or second membrane potential voltage can be 0 mV. Examples include −200 mV for the first membrane potential voltage, and 0 mV for the second membrane potential voltage. An additional example is 0 mV for the first membrane potential voltage, and 200 mV for the second membrane potential voltage. Specific examples of first membrane potential voltages and second membrane potential voltages can be independently selected from about −200 mV, about −180 mV, about −160 mV, about −140 mV, about −120 mV, about −100 mV, about −80 mV, about −60 mV, about −40 mV, about −20 mV, about 0 mV, about 20 mV, about 40 mV, about 60 mV, about 80 mV, about 100 mV, about 120 mV, about 140 mV, about 160 mV, about 180 mV, about 200 mV, and ranges between any two of these values.

Alternatively, more complicated voltage patterns can be used in the methods. The methods can further comprise exposing the targets to at least one step voltage prior to subjecting them to the depolarizing pulse at a second membrane potential voltage. The step voltage is an intermediate voltage between the first membrane potential voltage and the second membrane potential voltage. The step voltage can be used to measure leak subtraction. For example, a first membrane potential voltage of −80 mV, a step voltage of −50 mV, and a second membrane potential voltage of 20 mV can be used.

The depolarizing pulse can generally be applied for any length of time. For example, the depolarizing pulse can be applied for up to about 5000 seconds. Examples of the length of time include about 10 microseconds, about 1 milliseconds, about 10 milliseconds, about 100 milliseconds, about 1 second, about 2 seconds, about 3 seconds, about 4 seconds, about 5 seconds, about 10 seconds, about 20 seconds, about 30 seconds, about 40 seconds, about 50 seconds, about 60 seconds, about 70 seconds, about 80 seconds, about 90 seconds, about 100 seconds, about 500 seconds, about 1000 seconds, about 2000 seconds, about 3000 seconds, about 4000 seconds, about 5000 seconds, and ranges between any two of these values.

The one or more cells can generally be any type of cells which have a membrane and membrane potential. For example, the cells can be bacterial (Gram-positive or Gram-negative), eucaryotic, procaryotic, fungal, insect, avian, reptilian, oocyte, fly, zebrafish, nematode, fish, amphibian, or mammalian cells. The methods can also be used on non-cell materials such as artificial membranes, liposomes, and phospholipid bilayers. Examples of primary mammalian cells include human, mouse, rat, dog, cat, bear, moose, cow, horse, pig, or Chinese hamster ovary ("CHO") cells. Other examples of types of cells include immune system cells (e.g., B-cells, T-cells), oocytes, red blood cells, white blood cells, neurons, epithelial, glia, fibroblast, cancer cells, and immortalized cells.

The nanostructures can be introduced into the target by a number of methods. Examples of such methods include use of a patch pipette, passive or active uptake via endocytosis or other uptake mechanisms, electroporation, liposome-mediated delivery, pluronic block copolymer-mediated delivery, cell-penetrating peptide-mediated uptake, protein-mediated uptake, microinjection, transfection, viral delivery, optoporation, pore-forming substrates, membrane intercalators, or combinations thereof.

Methods of nanostructures loading into the cellular membrane (or other kinds of membranes mentioned above) include the immobilization of the nanostructures onto the supportive structures (for example, onto the bottom of a well in the microtiter plate) and subsequent addition of solution containing cells to an experimental chamber (such as a microtiter plate well).

The nanostructures can generally be any nanostructures. Examples of nanostructures include a nanocrystal, a film, a nanowire, a patterned substrate, and a mesh. Nanoparticles can generally be any nanoparticles. Semiconductor nanoparticles or nanocrystals typically have a semiconductor core, a shell, and optionally, one or more surface treatments. Semiconductor nanoparticles are commercially available from companies such as Quantum Dot Corp. (a wholly owned subsidiary of Invitrogen Corp.; Carlsbad, Calif.) and Evident Technologies (Troy, N.Y.). There also exist many published descriptions of the preparation of nanoparticles.

The semiconductor core and shell can independently be made of a material of an element from Group 2 or 12 of the Periodic Table of the Elements, and an element selected from Group 16 of the Periodic Table of the Elements. Examples of such materials include ZnS, ZnSe, ZnTe, CDs, CdSe, CdTe, HgS, HgSe, HgTe, MgS, MgSe, MgTe, CaS, CaSe, CaTe, SrS, SrSe, SrTe, BaS, BaSe, and BaTe. Alternatively, the semiconductor core and shell can independently be made of a material made of an element from Group 13 of the Periodic Table of the Elements, and an element from. Group 15 of the Periodic Table of the Elements. Examples of such materials include GaN, GaP, GaAs, GaSb, InP, InAs, and InSb. Alternatively, the semiconductor core and shell can independently be made of a material made of an element from Group 14 of the Periodic Table of the Elements. Examples of such a material include Ge, and Si. Alternatively, the semiconductor core and shell can independently be made of lead materials such as PbS or PbSe. The semiconductor core and shell can be made of alloys or mixtures of any of the above listed materials as well.

The semiconductor nanocrystal can generally be of any size (average diameter), but typically are about 0.1 nm to 1000 nm in size. More narrow ranges of sizes include about 0.1 nm to about 1 nm, about 1 nm to about 50 nm, and about 1 nm to about 20 nm. Specific size examples include about 0.1 nm, about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm, and ranges between any two of these values.

A typical single-color preparation of nanoparticles has crystals that are preferably of substantially identical size and shape. Nanocrystals are typically thought of as being spherical or nearly spherical in shape, but can actually be any shape. Alternatively, the nanocrystals can be non-spherical in shape. For example, the nanocrystal's shape can change towards oblate spheroids for redder colors. It is preferred that at least about 60%, at least about 70%, at least about 80%, at least about 90%, at least about 95%, and ideally about 100% of the particles are of the same size. Size deviation can be measured as root mean square of the diameter, with less than about 10% root mean square being preferred. Size deviation can be less than about 10% rms, less than about 9% rms, less than about 8% rms, less than about 7% rms, less than about 6% rms, less than about 5% rms, or ranges between any two of these values. Such a collection of particles is sometimes referred to as being "monodisperse".

It is well known that the color (emitted light) of the semiconductor nanocrystal can be "tuned" by varying the size and composition of the nanocrystal. Nanocrystals preferably absorb a wide spectrum of wavelengths, and emit a narrow wavelength of light. The excitation and emission wavelengths are typically different, and non-overlapping. The width of emission is preferably less than about 50 nm, and more preferably less than about 20 nm at full width at half maximum of the emission band (FWHM). Examples of emission widths (FWHM) include about 50 nm, about 40 nm, about 30 nm, about 20 nm, and about 10 nm. The emitted light preferably has a symmetrical emission of wavelengths. The emission maxima can generally be at any wavelength from about 200 nm to about 2000 nm. Examples of emission maxima include about 200 nm, about 400 am, about 600 nm, about 800 nm, about 1000 nm, about 1200 nm, about 1400 nm, about 1600 nm, about 1800 nm, about 2000 nm, and ranges between any two of these values.

Nanoparticles can also have a metal core, and in some cases, a surrounding shell structure. The metal core can be made from noble metals. Examples of such metals include silver, gold, and copper.

The nanoparticles can have surface coatings adding various functionalities. For example, the nanocrystals can be coated with lipids, phospholipids, fatty acids, polynucleic acids, polyethyleneglycol, primary antibodies, secondary antibodies, antibody fragments, protein or nucleic acid based aptamers, biotin, streptavidin, proteins, peptides, small organic molecules, organic or inorganic dyes, precious or noble metal clusters.

Alternatively, the nanoparticles can be made from a range of inorganic materials, including silicon, alumina, zirconia, ceria, yttria and oxides of tin and zinc. For example, silicon nanoparticles possess many of the advantageous features of compound semiconductor nanocrystals, such as size-tunable luminescence across the visible spectrum. In addition, silicon nanoparticles also low toxicity, high biocompatibility, efficient and stable surface functionalization, and potential low cost.

The use of nanoparticles in ion channel assays has multiple desirable features. Since nanoparticles have rapid response times, distinctive voltage dependencies are difficult to unintentionally inactivate, and the nanoparticles can provide a direct optical readout of voltage gradient changes across a membrane. The nanoparticles also possess other desirable qualities such as low toxicity, high photo-stability, the ability to be used in multiplexing applications, and their ability to be targeted using conjugated or otherwise associated materials.

Spectral characteristics of nanoparticles can generally be monitored using any suitable light-measuring or light-accumulating instrumentation. Examples of such instrumentation are CCD (charge-coupled device) cameras, video devices, CIT imaging, digital cameras mounted on a fluorescent microscope, photomultipliers, fluorometers and luminometers, microscopes of various configurations, and even the human eye. The emission can be monitored continuously or at one or more discrete time points. The photostability and sensitivity of nanoparticles allow recording of changes in electrical potential over extended periods of time.

Additional methods of assaying the emission from the nanostructure include measuring changes in light intensity, light polarization, light absorption, color of the emission, emission lifetime or half-life, or the "blinking" pattern.

An additional embodiment of the invention is directed towards nanoparticles coated with phospholipids. An example of such a nanocrystal is a commercially available phospholipid-coated Maple Red-Orange EviTag-T2 nanocrystal (Evident Technologies; Troy, N.Y.). There also exist published descriptions on preparation of lipid coated semiconductor nanocrystal materials.

Methods for the Excitation of Cells

An additional embodiment of the invention is directed towards the use of nanostructures to control the transmembrane potential of cells. Optical methods are attractive for use in biological applications due to their non-invasive nature and ease of use. For example, photo-induced electrical excitation of neuronal cells has been demonstrated using a film of semiconductor material (Frohmherz, P. and Stett, A., *Phys. Rev. Lett.* 75(8): 1670-1673 (1995); Starovoytov, A. et al., *J. Neurophysiol.* 93(2): 1090-1098 (2005)). Neuronal cells were attached to a thin film of a semiconductor material, achieving close contact of the extracellular membrane and the semiconductor surface. Illumination of the substrate with a laser beam has been shown to electrically excite the cells attached to the semiconductor surface.

Nanostructures such as nanoparticles exposed to light can act as a generator of a local electromagnetic field in their vicinity. The effect is believed to be due to creation of free charge carriers (electron-hole pairs upon illumination of nanoparticles) and consecutive charge separation. The currently proposed mechanism of action is electrostatic coupling of the cellular membrane and the surface of semiconductor, effectively forming a capacitor. When nanoparticles are placed in close proximity to a cell, the cumulative electromagnetic field generated by photo-excited nanoparticles will interact with the cellular transmembrane electrical gradient, resulting in an electromagnetic field that dictates the cellular membrane potential. Local depolarization of part of cellular membrane may be sufficient to generate depolarization in the whole cell.

In addition to use of the above described nanocrystals modified nanoparticles can be used to achieve a strong, stable, and controllable local electric field. Such modifications include high surface charge (e.g. CdTe/CdSe as core/shell combination), doping nanoparticles with materials that would act as donors or acceptors of one type of free charge carriers, creating nanoparticles with p- or n-type surface traps, conjugation of molecules that would contribute to a charge separation, and so on. Active generation of a cellular transmembrane potential can be achieved through use of nanoparticles that can convert light into electric power.

In conventional solar cells, electron-hole pairs are created by light absorption in a semiconductor core, with charge separation and collection accomplished under the influence of electric fields within the core.

As nanoparticles are approximately the same thickness as a cellular membrane, insertion into the membrane exposes the poles of the nanoparticle to both the extra- and intracellular space. Upon illumination with light, nanoparticles become a path for free charge carrier flow through the membrane, passing an electric current and in turn affecting the transmembrane potential. This way, voltage control over the cell could be achieved by changing, for example, the incident light's intensity and/or polarization.

Nanoparticles can be synthesized in shapes of different complexity such as spheres, rods, discs, triangles, nanorings, nanoshells, tetrapods, and so on. Each of these geometries have distinctive properties: spatial distribution of the surface charge, orientation dependence of polarization of the incident light wave, and spatial extent of the electric field. Non-uniform coating of nanoparticles with a dielectric material (such as phospholipids) can also help guide the free charge carriers from one side of the membrane to the other.

In order to manipulate free charge carrier concentration and mobility, nanoparticles can be doped with impurities such as indium, phosphorus, boron, and aluminum, and so on. A blend of nanoparticles and organic polymers may be advantageous for this application as nanoparticles are highly efficient in conducting electrons, whereas polymers are better at conducting holes. Functionalization of semiconductor nanoparticles with chromophores could also optimize this application by separating photon absorption from free charge carrier transport.

Accordingly, methods for the optical control of the transmembrane potential of a target can comprise providing at least one target, wherein the target is a cell or cellular fraction; contacting the target with at least one nanostructure under conditions suitable for interaction or insertion of the nanostructure with a cellular or subcellular membrane to prepare a treated target; delivering energy to the treated target; and detecting response of the target.

The cells can be any of the cells described above. The nanostructure can be any nanostructure including any of the nanostructures described above.

The conditions suitable for interaction or insertion can include a variety of methods. Examples of such methods include passive or active uptake via endocytosis, electroporation, liposome-mediated delivery, pluronic block copolymer-mediated delivery, cell-penetrating peptide-mediated uptake, protein-mediated uptake, microinjection, transfection, viral delivery, optoporation, pore-forming substrates, membrane intercalators, or combinations thereof.

The delivering energy can include delivering light, electrical energy, magnetic energy, and so on. The delivering energy step can be performed by essentially any illumination method, including laser illumination, mercury lamp illumination, xenon lamp illumination, halogen lamp illumination, LED illumination, and so on. An illuminating step is preferably performed at a wavelength or wavelength range suitable for absorption by the nanostructure.

The detecting step can be performed using a variety of methods using any suitable light-measuring or light-accumulating instrumentation. Examples of such instrumentation are a camera, a digital camera, a video camera, a CMOS camera, a CCD camera, a digital camera mounted on a fluorescent microscope, a photomultiplier, a fluorometer, a luminometer, a microscope, and even the human eye. The cellular response can be monitored continuously or at one or more discrete time points.

Alternatively, the detecting step can include use of a secondary detection mechanism. An example of such a secondary detection mechanism is the use of fluorescence resonance energy transfer ("FRET"). With FRET, the nanostructure can transfer its energy to a second molecule that then emits a detectable signal. Additional secondary detection mechanisms rely on changes in a cell that can be independently detected. For example, the cell may undergo lysis. Alternatively, the cell may undergo a chemical change, increasing or decreasing the concentration of one or more chemical or biochemical agents that can be independently measured.

At least one additional material can be added to the at least one cell or to the treated cell to assay the cellular response to the additional material. For example, the cell can be first contacted with the at least one nanoparticle, illuminated, and the cellular response detected as a "control" sample. The treated cell can then be contacted with the additional material to prepare a material-treated cell, illuminated, and detected. This second cellular response can be compared with the first (control) cellular response. A difference between the first cellular response and the second cellular response would indicate whether the addition of the material had any effect on cellular behavior. A different additional material, or an additional dose of the same additional material, can be added, followed by illumination and detection of a third cellular response. This can be done in a serial manner any number of times. For example, increasing dosages of a material can be detected, resulting in a third cellular response, a fourth cellular response, a fifth cellular response, a sixth cellular response, and so on. These serial cellular responses can be plotted or otherwise compared, and the effects of the serial treatments can be determined.

Alternatively, "control" and "test" samples can be performed in parallel. For example, a first cell can be contacted with a nanoparticle, illuminated, and the control cellular response detected. In parallel, either serially or simultaneously, a second cell can be contacted with a nanoparticle and a test material, illuminated, and the test cellular response detected. The control cellular response and the test cellular response can be compared.

The at least one additional material can generally be any material. Examples of such materials include drug candidates, modulators of cellular function, molecular moieties for enhanced drug delivery, molecular probes candidates, and so on.

Assay Materials

An additional embodiment of the invention is directed towards one or more containers having a layer of nanostructures deposited on one or more surfaces. For example, the container can be a test tube, centrifuge tube, or microtiter plate (e.g., 96 or 384 well plate). The entire inner surface of the tube or plate's wells can be coated with the nanostructures mentioned above. Alternatively, the lower or bottom inner surface of the tube or wells can be coated with the nanostructures. These assay materials can be stored for subsequent use with cells or other biological or artificial membrane materials.

The following examples are included to demonstrate preferred embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Preparation of Cells on Coverslips

Experiments were performed on A431 (a human cell line from an epidermoid carcinoma) cells or CHO (Chinese hamster ovary) cells stably expressing M1 muscarinic $G_q$-protein coupled receptor using nanoparticles commercially available from Quantum Dot Corp. (a wholly owned subsidiary of Invitrogen Corp.; Carlsbad, Calif.) and Evident Technologies (Troy, N.Y.). The intracellular (pipette) solution (pH 7.3) was composed of 1.40 mM CsCl, 10 mM EGTA, 10 mM HEPES. The extracellular solution (pH 7.4) was composed of 140 mM NaCl, 5 mM KCl, 1.8 mM $CaCl_2$, 1 mM $MgCl_2$, 10 mM EGTA, 10 mM glucose, 10 mM HEPES.

In experiments with extracellular delivery of nanoparticles, several types of commercially available nanocrystals were used. In one series of experiments, streptavidin-functionalized QD605 (Quantum Dot Corp.) in the buffer solution B from the QDot® kit were added to extracellular solution in concentrations from 25 to 500 µg/ml. In another experimental series, non-functionalized Maple Red-Orange EviTag-T2 (Evident Technologies, Troy, N.Y.) were used in the same concentrations.

For experiments with intracellular applications of nanoparticles, streptavidin-functionalized QD605 (Quantum Dot Corp.) were added to the pipette solution in concentrations from 25 to 500 µg/ml.

Glass 18 mm round coverslips with cells plated on the surface were transferred into a special chamber 508SW (ALA Scientific Instruments, Westbury, N.Y.). Control extracellular solution was substituted with semiconductor nanocrystal-containing extracellular solution. After 30 minutes at room temperature, the coverslips with cells were washed with PBS solution until excess free-floating nanocrystals were removed. To visually confirm that washing had removed all free-floating nanoparticles, coverslips were placed under the microscope. If excitation was seen by the naked eye, the washing procedure was repeated two more times.

After the washing procedure was completed, the coverslip was mounted in a microscope chamber and the cells were maintained in buffered EBSS solution during the experiment. Only cells labeled with nanoparticles were chosen for further experiments.

Example 2

Use of Patch Pipette

Glass micropipettes for patch-clamp experiments were pulled from borosilicate glass capillaries (1.2 mm no-capillary glass, Sutter Instruments; Novato, Calif.) using a Sutter 2000™ pipette puller (model Sutter 2000; Sutter Instruments; Novato, Calif.) using the prerecorded 4-step patch pipette pulling protocol. The open diameter of the pipette tip was 1.5-2.2 µm with a resistance of 2-3 MΩ. The micropipettes were filled with intracellular solution.

Experiments were performed at room temperature in whole-cell patch-clamp configuration using a Axopatch200B patch-clamp amplifier (Molecular Devices; Sunnyvale, Calif.). After successful giga-seal formation, brief pulses of suction were used to rupture the cellular membrane to achieve whole-cell patch-clamp configuration.

The following test protocol was used for cell stimulation. The membrane potential was set at −70 mV. A depolarizing pulse necessary to take the cell to +40 mV was applied to the interior of the cell for 2 seconds, followed by returning the membrane potential to −70 mV.

Example 3

External Loading of Streptavidin-Coated Nanoparticles

The emission intensity of externally applied streptavidin-functionalized nanoparticles occurring in response to voltage stimulation of the cell (QD605-streptavidin, Quantum Dot Corp.) was visualized using a cooled CCD Optronics Tec 470 camera (Optronic Engineering, Goleta, Calif.) linked to a computer. Voltage changes elicited across the cellular membrane via patch pipette attached to a cell did not result in changes in the emission intensity of these particular nanoparticles. Nine cells were tested in this series, and none exhibited changes in emission intensity to the voltage stimulation protocol described in the previous example. The streptavidin coating of the nanoparticles used in this example may have prevented the nanocrystals from being strategically placed inside the cellar membrane, the site of the highest membrane gradient. The streptavidin coating of the nanoparticles used in this example may have prevented the nanocrystals from associating with the cellular membrane in such a way that they could effectively monitor the voltage gradient across the membrane.

Example 4

Intracellular Loading of Nanoparticles

This example was designed to test the emission of nanoparticles loaded intracellularly in response to a voltage change across the cellular membrane.

It is preferred to position the nanoparticles in close proximity to the cellular membrane in order to achieve modulation of optical signal by voltage. Since the main part of the voltage gradient exists across the cytoplasmic membrane, the nanoparticles located close to the membrane would be exposed to a significant portion of the total electrical gradient.

Example 5

Protocol for Intracellular Loading of Nanoparticles

Nanoparticles were added to the patch pipette solution at a concentration of 200 Initial experiments were performed using streptavidin-coated nanoparticles QD605 (Quantum Dot Corp.). A431 cells, plated on glass 18 mm round coverslips were placed into the electrophysiology chamber mounted on a Zeiss Axiovert 100 microscope.

After establishing a whole-cell patch-clamp configuration, several brief pulses of positive pressure were applied to the pipette interior. These small changes of intra-pipette pressure were used to facilitate cell perfusion with the intracellular semiconductor nanocrystal-containing solution. Voltage stimulation experiments on the cells were conducted after loading of nanocrystals was achieved.

The following test protocol was used for cell stimulation. The membrane potential was set at −70 mV. A depolarizing pulse of +40 mV was applied to the interior of the cell for 1 to 2 seconds, and subsequently the membrane potential was returned to −70 mV.

Emission of the nanoparticles was recorded constantly during voltage stimulation of the cell using a CCD Optronic Tec 470 camera (Optronic Engineering; Goleta, Calif.). The effects of the voltage stimulation on emission intensity of nanoparticles are shown in FIG. 1. Ten of twelve cells responded to the voltage stimulation protocol, as evidenced by a change in semiconductor nanocrystal emission intensity. Thus, the nanoparticles were able to respond to the changes in transmembrane potential by changing their optical characteristics.

Example 6

Use of Treated Semiconductor Nanoparticles as Voltage Sensors

One prospective use for semiconductor nanoparticle-based membrane potential-sensitive assays is high throughput screening for drug discovery. One of the major challenges for HTS assays is the ease of voltage indicator loading into cells. Phospholipid-coated quantum dots were selected as an example of a surface-modified nanoparticle for these experiments.

In this example, modified nanoparticles (phospholipid-coated EviTag-T2 (Evident Technologies, Troy, N.Y.)) were applied to A431 cells externally. Cells attached to 18 mm round coverslips were incubated for 45-60 minutes in an extracellular solution containing nanoparticles at 25 to 500 µg/ml.

After incubation, the coverslips and attached cells were placed into a special chamber 508SW (ALA Scientific Instruments, Westbury, N.Y.) on an Zeiss Axiovert 100 microscope, equipped with a CCD camera for optical recordings. After establishing a whole-cell patch-clamp configuration as described previously, voltage stimulation experiments were performed.

The following test protocol was used for cell stimulation. Membrane potential was set at −70 mV. A depolarizing pulse of +40 mV was applied to the interior of the cell for 1 to 2 seconds, and then the membrane potential was returned to −70 mV.

Figure 2:
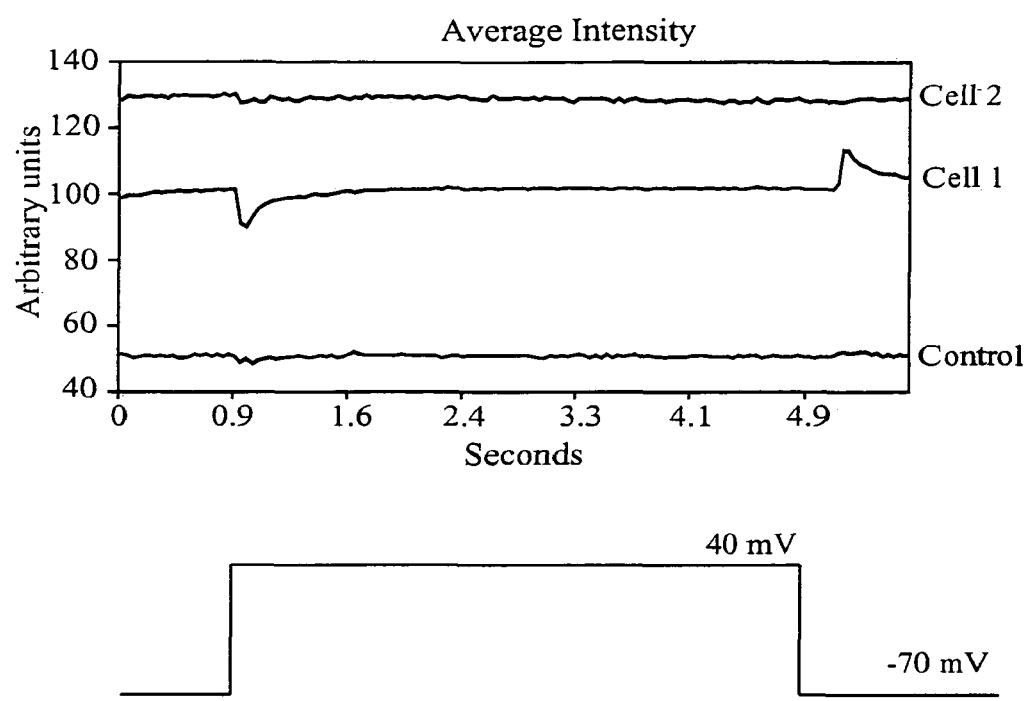
FIG. 2 shows the effect of electrophysiological stimulation on cells containing intracellular lipid-modified nanoparticles. The upper traces show the change in fluorescence intensity of phospholipid-functionalized semiconductor nanocrystals in response to change in transmembrane potential using the patch-clamp method from three areas of interest (2 cells and background). Cell #1 was exposed to voltage stimulation, while cell #2 was not exposed to voltage stimulation. Semiconductor nanocrystals were applied to the extracellular side of the cellular membrane. The lower trace represents the corresponding voltage stimulation protocol along the same time scale.

Emission of the nanoparticles was recorded during voltage stimulation of the cell using a CCD Optronic Tec 470 camera (Optronic Engineering, Goleta, Calif.). The effects of the electrophysiological stimulation are shown in FIG. 2. Of the 8 cells tested under these experimental conditions, 6 cells responded to the voltage stimulation protocol by transiently changing their emission intensity.

These results suggest that nanoparticles having a hydrophobic phospholipid coating can localize in or on the cellular membrane, and therefore, are able to report on the cellular voltage potential. This method of loading the voltage-sensing nanoparticles represents an especially advantageous means to prepare cells for high throughput screening.

Example 7

Summary of Results from Examples 1-6

These results demonstrate that nanoparticles can be used as a self-contained fluorescent voltage indicator. The nanoparticles can be used as a direct optical detection system for changes of the voltage gradient across a membrane. Optimization of delivery and surface modifications can further improve the usefulness of the nanoparticles in the above described methods.

Example 8

Patch-Clamp Recordings from Optically Excited Cells

Cells having an expressed ion channel target can be prepared using established cell culture preparation procedures. CHO or A431 cells, plated on round glass 18 mm coverslips will be incubated with a solution containing nanoparticles at appropriate concentrations for 15-60 minutes at room temperature. After the incubation, the coverslips will be washed four times with PBS solution.

Alternatively, glass coverslips or plate wells can be pre-coated with the nanoparticles allowing cells to be seeded on top of the nanoparticle layer. Wells of the plate will be filled with nanoparticle-containing solution at the appropriate concentration. The plate can be stored for several hours under the sterile conditions.

After the nanoparticles-containing solution is washed away, the coverslip will be transferred into a special microscope chamber 508SW (ALA Scientific Instruments, Westbury, N.Y.) and maintained in buffered EBSS solution during the experiment.

Glass micropipettes for patch-clamp experiments will be pulled from borosilicate glass capillaries (Sutter 1.2 mm no-capillary glass) using a Sutter 2000™ pipette puller (model Sutter 2000, Sutter instruments, Novato, Calif.) using a prerecorded 4-step patch pipette pulling protocol. The open diameter of the pipette tip will be 1.5-2,2 µm.

The micropipettes will be filled with a solution containing 140 mM potassium aspartate, 5 mM NaCl, and 10 mM HEPES (pH 7.35). Voltages and currents will be recorded at room temperature using a Axopatch 200B patch-clamp amplifier (Molecular Devices; Sunnyvale, Calif.).

After establishing the successful Giga-seal, brief pulses of suction will be used to rupture the cellular membrane to achieve whole-cell patch-clamp configuration. The following test protocol will be used for cell stimulation. Brief pulses of excitation light (emitted by laser, or by other light source) will be used to illuminate the patched cell. Voltage and current changes through the cellular membrane will be recorded in the whole-cell configuration.

Example 9

Optical Recordings from Optically Excited Cells

Cells having an expressed ion channel target can be prepared using established cell culture preparation procedures. CHO or A431 cells, plated on round glass 18 mm coverslips will be incubated with a voltage sensitive dye (e.g., a semiconductor nanoparticles-based voltage sensor) for 15-60 minutes. After the incubation, the coverslips will be washed four times with PBS solution.

The second step will be an incubation of tested cells with a solution containing nanoparticles at an appropriate concentration for 15-60 minutes at room temperature. After the incubation, the coverslips will be washed four times with PBS solution. After the nanoparticle solution is washed away, the coverslip will be mounted on a microscope chamber and maintained in buffered EBSS solution during the experiment.

Alternatively, glass coverslips or plate wells can be pre-coated with the nanoparticles allowing cells to be seeded on top of the nanoparticle layer. Wells of the plate will be filled with nanoparticle-containing solution at the appropriate concentration. The plate can be stored for several hours under the sterile conditions.

Alternatively, at the beginning of experiment the cell suspension will be incubated with specially prepared suspension of semiconductor nanoparticles. After incubating for 5-60 minutes, the cells will be dispensed into wells of a microtiter plate (e.g., a 96, 384, or 836 well plates). The microtiter plates will be mounted on the microscope stage for the experiment.

Voltage stimulation will be achieved by illuminating the cell suspension with brief pulses of excitation light (emitted by laser, or by other light source). Emission of the nanoparticles will be recorded during voltage stimulation of the cell using a cooled CCD camera (e.g., Optronics Tec 470 (Optronic Engineering; Goleta, Calif.) or XR/MEGA-10Z™ fast camera (Stanford Photonics, Inc.; Palo Alto, Calif.)) linked to a computer.

The emission pattern change of the nanoparticles will indicate the cellular response to excitation by photo-activated nanoparticles on the cell surface.

Example 10

First Preparation Method for Target Cells in Microplate Wells

A solution containing non-functionalized Maple Red Evi-Tag-T2 (Evident Technologies, Troy, N.Y.) or streptavidin-functionalized QD605 nanocrystals (Quantum Dot Corp.) at various concentrations were added to the 96-well Microplates (Nunc; Denmark). The pretreated plates were stored under sterile conditions for six hours, allowing the solution to dry, and leaving the layer of nanoparticles on the bottom of the wells.

Experiments were performed on CHO cells stably expressing M1 muscarinic $G_q$-protein coupled receptor. A suspension of cells was added to the plates and incubated for 12-24 hours at 37° C. in the presence of carbon dioxide.

After the incubation, the plates with cells were washed with PBS solution until any excess free-floating cells and nanocrystals had been removed. To confirm that washing had removed all free-floating nanoparticles, plates were visually inspected with a microscope. If excitation was seen by the naked eye, the washing procedure was repeated two more times. After washing, the pates were transferred into PathWay™ screening station (BD Biosciences; San Jose, Calif.) for evaluation.

Example 11

Second Preparation Method for Target Cells in Microplate Wells

Cells were plated in 96-well plates. Plates were either glass-bottomed or poly-L-lysine-coated (Nunc; Denmark). Maple Red EviTag-T2 nanoparticles were added to the cell-containing solution. Cells were incubated in the presence of nanoparticles for 15-60 minutes. Any excess nanoparticles were washed away. Plates with nanoparticle-treated cells were placed inside an environmentally controlled chamber of Pathway HT machine (BD Biosciences; San Jose, Calif.).

The series of images of cells from each well were acquired in kinetic mode from several wells consecutively. First ten images in the series were taken as control images to ensure the stability of a signal from labeled cells. The following step was an application of potassium chloride solution into a well. Concentration of potassium chloride solution was chosen to achieve the final potassium chloride concentration of 100 mM thus shifting the membrane potential of cells (to about 0 mV) in depolarizing direction. The optical response of nanocrystal-labeled cells to depolarization stimuli for each individual well was recorded using Pathway HT machine (BD Biosciences; San Jose, Calif.).

After the assays, a series of images were processed using MethaMorph software (Molecular Devices, Sunnyvale, Calif.). Regions of interest were chosen either around the cellular membrane or in extracellular space (control).

Example 12

Sensitivity of Externally Applied Nanoparticles to Changes in Cellular Membrane Potential Detected by High Content Screening CHO cells stably expressing M1 muscarinic $G_q$-protein coupled receptors were plated in 96-well microplates, either glass-bottomed or poly-L-lysine-coated (Nunc; Denmark). Maple Red EviTag-T2 nanoparticles were added to the cell-containing solution. Cells were incubated in the presence of nanoparticles for 15-60 minutes. Any excess nanoparticles were washed away. Plates with nanoparticle-treated cells were placed inside an environmentally controlled chamber of a Pathway HT™ screening station (BD Biosciences; San Jose, Calif.).

A series of images of cells from each well were acquired in a kinetic mode from several wells consecutively. First, several images in the series were taken as control images to ensure the stability of a signal from labeled cells. Next, potassium chloride solution was added into the well. The concentration of potassium chloride solution was selected to achieve the final potassium chloride concentration of 100 mM, thus shifting the membrane potential of cells in a depolarizing direction. The optical response of nanocrystal-labeled cells to depolarization stimuli for each individual well was recorded using a Pathway HT™ screening station (BD Biosciences; San Jose, Calif.).

After the experiments, the series of images was processed using MethaMorph software (Molecular Devices, Sunnyvale, Calif.). Regions of interest (ROI) were selected either around the cellular membrane or in the extracellular space (control).

Depolarization of cells by extracellular application of potassium chloride resulted in transient decrease in optical signal from cells. It should be noted that optical signal from extracellular space exhibited some intensity decrease as well. However, the effect of potassium chloride application in cells was significantly higher. For example, in one experiment, change in the maximum response in cellular membrane from 12 cells was 349±56 AU, whereas signal intensity change for extracellular space was only 191±38 AU (3 ROIs).

Figure 3:
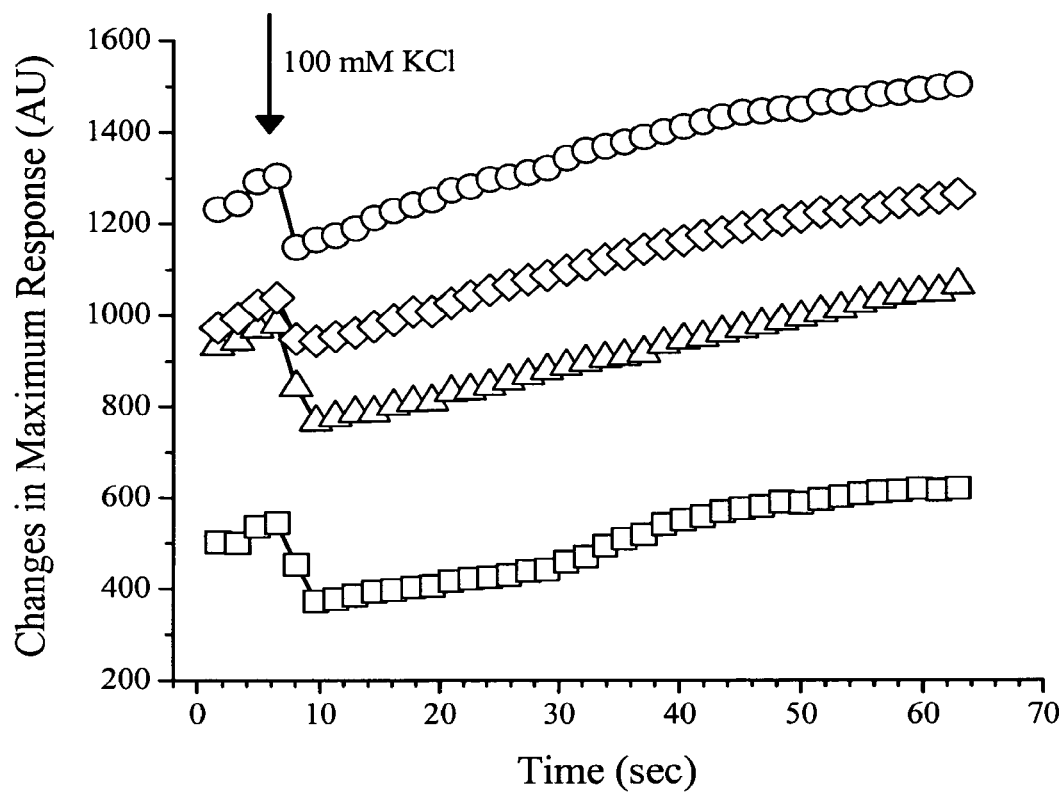
FIG. 3 shows the results of monitoring transient changes in cells caused by addition of a high concentration of potassium chloride (100 mM). The circle, diamond, triangle, and square symbols represent different regions of interest (ROI).

On average, background-subtracted signal intensity in cells decreased 17.4±5.1% (number of experiments=8). FIG. 3 represents an example of transient changes in emission intensity from several cells one well in response to cells' exposure to potassium chloride in high concentration.

These results demonstrate that changes in the amplitude of optical signal emitted by nanoparticles associated with the cellular membrane reflects changes in membrane potential, and confirm that nanoparticles can act as a sensor of cellular membrane potential.

All of the compositions and/or methods and/or processes and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. AU such similar substitutes and modifications apparent to those skilled in the art are deemed to be within the scope and concept of the invention.

What is claimed is:

1. A method for assaying changes in transmembrane potential, the method comprising:
providing at least one target, wherein the target is a cell, cellular fraction, or artificial membrane structure;
contacting the target with at least one semiconductor nanocrystal to form a treated target, wherein each nanocrystal further comprises a hydrophobic surface coating;
stimulating the treated target, such that the transmembrane potential of the target changes, wherein the at least one semiconductor nanocrystal emits light in direct response to a voltage fluctuation resulting from the change in transmembrane potential of the target, wherein the light is directly emitted from the at least one semiconductor nanocrystal without transfer of energy to a second molecule that then emits an optical signal;
assaying emission by detecting the directly emitted light from the at least one semiconductor nanocrystal; and
correlating the emission with the change in transmembrane potential.

2. The method of claim 1, wherein the contacting step comprises introducing the at least on semiconductor nanocrystal into the target.

3. The method of claim 1, wherein the contacting step comprises introducing the at least one semiconductor nanocrystal into a cellular membrane of the target.

4. The method of claim 1, wherein the contacting step comprises introducing the at least one semiconductor nanocrystal onto or near a cellular membrane of the target.

5. The method of claim 1, further comprising assaying emission from the at least one semiconductor nanocrystal after the contacting step but before the stimulating step.

6. The method of claim 1, wherein the stimulating step comprises electrical stimulation, magnetic stimulation, chemical stimulation, biological stimulation, contacting the target with a drug suspected of being able to activate ion channels, contacting the target with a drug suspected of being able to inhibit ion channels, or combinations thereof.

7. The method of claim 6, wherein the electrical stimulation comprises use of a patch clamp, or application of an external electric field.

8. The method of claim 6, wherein the chemical stimulation comprises contacting the target with a potassium salt or a sodium salt.

9. The method of claim 6, wherein the biological stimulation comprises contacting the target with a compound that can modify ion channel activity.

10. The method of claim 1, wherein the stimulating step comprises maintaining the target at a first membrane potential voltage, depolarizing or hyperpolarizing the target to a second membrane potential voltage, and returning the target to the first membrane potential voltage.

11. The method of claim 1, wherein the cell is a eucaryotic cell, a procaryotic cell, bacterial cell, a Gram-positive bacterial cell, a Gram-negative bacterial cell, a fungal cell, an insect cell, an avian cell, a reptilian cell, an oocyte, a fly cell, a zebrafish cell, a nematode cell, a fish cell, an amphibian cell, or a mammalian cell.

12. The method of claim 1, wherein the cell is a eucaryotic cell.

13. The method of claim 1, wherein the cellular fraction is a nucleus, a ribosome, a mitochondria, an endoplasmic reticulum, a Golgi apparatus, a vacuole, a synaptic vesicle, or a lysosome.

14. The method of claim 1, wherein the artificial membrane structure is a phospholipid micelle.

15. The method of claim 1, wherein at least one semiconductor nanocrystal is a core-shell nanocrystal.

16. The method of claim 1, wherein the stimulating step comprises stimulating the treated target with light.

17. The method of claim 1, further comprising monitoring transient changes in cell membrane potential.

18. A method for assaying changes in transmembrane potential, the method comprising:
providing at least one cell;
contacting the cell with at least one semiconductor nanocrystal to form a treated cell, wherein the nanocrystal further comprises a hydrophobic surface coating;

stimulating the treated cell with light, such that the transmembrane potential of the cell changes and the at least one semiconductor nanocrystal emits light in direct response to the stimulation resulting from the voltage fluctuation from the change in transmembrane potential of the cell, wherein the light is directly emitted from the at least one semiconductor nanocrystal without transfer of energy to a second molecule that then emits an optical signal;

assaying emission by detecting the directly emitted light from the nanocrystal; and correlating the emission with the change in transmembrane potential.

* * * * *